United States Patent [19]

Wissner et al.

[11] 4,300,004

[45] Nov. 10, 1981

[54] PROCESS FOR THE PREPARATION OF DICHLOROBENZENES

[75] Inventors: Adolf Wissner, Leverkusen; Werner Hauser, Odenthal-Gloebusch; Feliks Bitners; Raimund Wambach, both of Leverkusen, all of Fed. Rep. of Germany

[73] Assignee: Bayer Aktiengesellschaft, Leverkusen, Fed. Rep. of Germany

[21] Appl. No.: 102,178

[22] Filed: Dec. 10, 1979

[30] Foreign Application Priority Data

Dec. 23, 1978 [DE] Fed. Rep. of Germany ....... 2855940

[51] Int. Cl.$^3$ ............................................. C07C 25/00
[52] U.S. Cl. ..................................... 570/211; 203/48
[58] Field of Search .................... 260/650 R; 570/211; 203/48

[56] References Cited

U.S. PATENT DOCUMENTS 2,527,606  10/1950  Webb ............................ 260/650 R Primary Examiner—Curtis R. Davis Attorney, Agent, or Firm—Sprung, Felfe, Horn, Lynch & Kramer

[57] ABSTRACT

A process for separating ortho-, meta-, and/or para-dichlorobenzene from an isomeric mixture thereof which comprises:
  A. in a first step, distilling said isomeric mixture to distill over meta- and/or para-dichlorobenzene to leave behind ortho-dichlorobenzene which is separated off as bottoms product;
  B. in a second step, cooling the distillate from step A to a temperature of 10° to 40° C. whereby para-dichlorobenzene as a solid phase is obtained and separating said solid phase from liquid phase with which it is in admixture;
  C. in a third step, further cooling said liquid phase from step B to a temperature of −40° to −5° C. whereby to precipitate a second solid phase and separating said second solid phase from the liquid phase with which it is in admixture;
  D. in a fourth step, distilling the liquid phase from step C whereby to obtain an isomeric mixture as bottoms and an isomeric mixture as distillate; and
  E. removing m-dichlorobenzene from the distillate of step D.

5 Claims, No Drawings

PROCESS FOR THE PREPARATION OF DICHLOROBENZENES

The invention relates to a process for the preparation of ortho-, meta- and/or para-dichlorobenzene by separating an isomer mixture containing the dichlorobenzenes.

In the chlorination of benzene or monochlorobenzene to give dichlorobenzene, a mixture of the three dichlorobenzene isomers is, as a rule, formed, in addition to impurities which contain more than or less than two chlorine atoms on the benzene nucleus. In general, the impurities can easily be separated off since they generally have considerably different physical properties to the dichlorobenzene (German (BRD) Offenlegungsschrift No. 2,332,889).

On the other hand, separation of the individual dichlorobenzenes is difficult since their physical properties are very similar.

It is particularly difficult to separate off the meta-compound, which has virtually the same boiling point as the para-compound, so that distillation according to German (BRD)Offenlegungsschrift No. 2,332,889 is said to be ineffective. Separation processes by fractional crystallisation can hardly be carried out since eutectic mixtures are formed German (BRD) Offenlegungsschrift No. 2,332,889.

To solve this separation problem, it is known first to brominate the isomer mixture according to U.S. Pat. No. 3,170,961, then to separate the mixture by distillation and afterwards to debrominate the products again. This process is very expensive and is associated with high losses during the separation.

A further separation process with the aid of molecular sieves (U.S. Pat. No. 2,958,708) is likewise inadequate because of the difficulties during regeneration of the molecular sieve and because of the high costs.

According to the process of German (BRD) Offenlegungsschrift No. 2,332,889, separation of the dichlorobenzene isomer mixture is effected with the aid of extractive distillation in the presence of aprotic solvents, the dielectric constant of which is greater than 20 and the dipole moment of which is less than 3.0 Debyes. Hexamethylphosphoric acid triamide is mentioned as a suitable solvent in therein but is toxicologically unacceptable when used (CuEN 17 (1975) and CuEN 3 (1976)). The other solvents mentioned in German Offenlegungsschrift No. 2,332,889 have a considerably lower coefficient of relative volatility than meta- and para-dichlorobenzene. This entails a substantially greater separation effort. A further disadvantage of extractive distillation of dichlorotoluenes is the necessity for special columns which, because of the low value for the relative volatility, must have a large number of trays and at the same time a low pressure loss per tray. As indicated in German Offenlegungsschrift No. 2,332,889, these columns contain geometrically shaped mesh packing of metal. In the distillation of chlorinated compounds, corrosion, especially of mesh packing of sheet iron or iron alloys, cannot be avoided.

SUMMARY OF THE INVENTION

In accordance with this invention, there is provided a process for separating ortho-, meta- and/or para-dichlorobenzene from an isomeric mixture thereof which comprises:

A. in a first step, distilling said isomeric mixture to distill over meta- and/or para-dichlorobenzene to leave behind ortho-dichlorobenzene which is separated off as bottoms product;

B. in a second step, cooling the distillate from step A to a temperature of 10 to 40° C whereby paradichlorobenzene as a solid phase is obtained and separating said solid phase from liquid phase with which it is in admixture;

C. in a third step, further cooling said liquid phase from step B to a temperature of −40 to −5° C whereby to precipitate a second solid phase and separating said second solid phase from the liquid phase with which it is in admixture;

D. in a fourth step, distilling the liquid phase from step C whereby to obtain an isomeric mixture as bottoms and an isomeric mixture as distillate; and E. removing m-dichlorobenzene from the distillate of step D.

The distillate from the fourth step, step D, can be treated to recover meta-dichlorobenzene therefrom as a solid. To recover solid meta-dichlorobenzene, the distillate is cooled to a temperature of −25 to −40° C whereby to precipitate solid meta-dichlorobenzene. The solid can be separated off and the remaining liquid can be fed to the distillation of step D.

In accordance with another embodiment of this invention, the isomeric mixture obtained as overhead from the distillation of step D, the fourth step can be further distilled to obtain as further distillate meta-dichlorobenzene overhead. The bottoms from this further distillation can be recycled into step D, the fourth step of the process. Generally speaking, this further distillation, which constitutes an alternative fifth step of the invention, can be effected using distillation columns having between 70 and 400 trays.

Isomer mixtures which contain ortho-, meta- and/or para-dichlorobenzene can be separated by the process according to the invention. The amounts of the individual isomers in the mixture can vary within wide limits. Traces of the isomers can be separated off with the aid of the process. However, it is appropriate to use as starting materials isomer mixtures which contains at least 0.2% by weight of a particular isomer. Mixtures which contain at least 2% by weight a particular isomer can preferably be employed.

Isomer mixtures of dichlorobenzene are obtained, for example, by known processes by chlorination of benzene or monochlorobenzene (Ullmann, Encyklopädie der techn. Chemie" (Encyclopaedia of industrial Chemistry"), volume 9, 4th edition, pages 504–507 A(1975), and Winnacker-Küchler, Chemische Technologie (Chemical Technology), volume 3, 2nd edition (1959) pages 800/801).

It is also possible to obtain, by isomerization of dichlorobenzene, a dichlorobenzene mixture, largely free from compounds which are monochlorinated and trichlorinated or more highly chlorinated.

The by-products formed during the preparation of dichlorobenzenes, such as monochlorobenzene or benzenes which are trichlorinated and more highly chlorinated, are appropriately largely separated off before carrying out the separation according to the invention. In general, a starting mixture which essentially contains only dichlorobenzene (over 99%) is obtained by simple distillation. However, it is also possible to work up a dichlorobenzene isomer mixture which also contains benzenes which are trichlorinated and more highly chlorinated with the aid of the separation according to the invention.

In the first step of the process according to the invention, most of the ortho-dichlorobenzene is separated off using a distillation column. In general, this distillation is carried out in a column with 130 to 250 trays, preferably 180 to 220 trays, and during this distillation a mixture of meta- and paradichlorobenzene which can contain at most 2% by weight of ortho-dichlorobenze passes over the top. If benzenes which are trichlorinated and more highly chlorinated are present, these by-products are separated off with the o-dichlorobenzene. Isolation of pure o-dichlorobenzene is then effected in a further distillation.

In the second step of the proccess according to the invention, the isomer mixture obtained over the top of the distillation column in the first step of the process according to the invention is cooled to a temperature in the range from 10 to 40° C. The temperature range from 30° to 40° C. is preferred. Pure p-dichlorobenzene crystallizes out as a solid phase and is separated off.

The liquid phase in the second step of the process according to the invention is cooled to a temperature in the range from $-5°$ to $-40°$ C. in a third step. The temperature range from $-20°$ to $-30°$ C. is preferred. The phase which precipitates during this procedure is admixed to the isomer mixture for the crystallization in the second step.

The liquid phase remaining in the third step of the process according to the invention is passed, in a fourth step, to a distillation. This distillation is carried out with a tray column with 70 to 400 trays, preferably 200 to 300 trays.

One can use, for example, columns with at least 100 actual trays in the separation by distillation. An isomer mixture which is admixed to the starting isomer mixture for the first step of the process according to the invention is obtained at the bottom of the distillation column.

An isomer mixture is obtained over the top of the separation by distillation in the fourth step of the process according to the invention and is cooled to a temperature in the range from $-20°$ to $-40°$ C. in a fifth step. The temperature range from $-25°$ to $-30°$ C. is preferred.

Pure m-dichlorobenzene is obtained as a solid phase in this step. The liquid phase is added to the second distillation of the process according to the invention (fourth step). The crystallization steps 2, 3 and 5 can, of course, also be divided into several individual steps.

The crystallization steps 2, 3 and 5 of the process according to the invention can be carried out in commercially available crystallization apparatuses, preferably in tube crystallizers which operate free of solvents.

Likewise, commercially available distillation columns can be employed for distillation steps 1 to 4 of the process according to the invention without particular requirements with regard to column construction. Tray columns are appropriately used. The columns can be steel bubble-cap tray columns.

In the process according to the invention, it is possible to obtain, in an advantageous manner, the isomers of dichlorobenzene quantitatively and without losses by the separation process. The dichlorobenzenes thus obtained are virtually free from other isomers.

If the dichlorobenzene isomer mixture employed consists of less than 3 isomers, it is, of course, possible to leave the separation step corresponding to the missing isomer out of the process according to the invention.

Since it is indicated in German Offenlegungsschrift No. 2,332,889 that simple distillation is ineffective in practice for the separation of meta- and para-dichlorobenzene because the boiling points of meta-dichlorobenzene and of para-dichlorobenzene are very close to one another and also crystallization leads only to a eutectic mixture, it was surprising and not to be foreseen that not only a 2-substance mixture (meta-/para-dichlorobenzene) but also a 3-substance mixture, namely meta-dichlorobenzene, para-dichlorobenzene and ortho-dichlorobenzene, can be separated via a combination of distillation and crystallization so that virtually pure meta-dichlorobenzene is obtained.

Relatively cheap tray columns which are far less susceptible to corrosion then the columns with mesh packing or geometrically shaped gauzes required in the above discussed German Offenlegungsschrift can be used for the distillation steps of the process according to the invention. It is known that it is precisely the chlorinated aromatics which are corrosive due to the presence of small amounts of impurities, especially if slight traces of water are present. Even after drying the dichlorobenzene isomer mixture, small amounts of water can penetrate into the distillation column with air from the atmosphere through leaks and can cause corrosion. A further advantage of the present process is that virtually no losses or residues occur during working up.

The process is to be regarded as non-polluting. A further advantage is that no auxiliaries such as bromine or aprotic polar solvents are required. Another advantage is that ortho-dichlorobenzene does not have to be separated off completely in the first separation stage of the process according to the invention. Because of the combination of crystallization and distillation, the dimensions of the apparatus can be kept as small as possible.

Dichlorobenzenes are intermediate products, for example for dyestuffs, aroma substances, pharmaceuticals, plant protection agents and disinfectants, and solvents for lacquers, oils, waxes, resins and the like and they can be used in the chemical industry as reaction media (Ullmanns "Enzykolpädie der techn. Chemie" ("Encyclopaedia of industrial Chemistry"), 4th edition, volume 9, page 509 (1975), and Winnacker-KUM/u/ chler, Chemische Technologie (Chemical Technology), volume 3, 2nd edition (1959), page 820).

EXAMPLE

A dichlorobenzene mixture obtained in the chlorination of benzene, after separating off chlorobenzene and lower-boiling compounds by distillation, contains 2.5% by weight of m-dichlorobenzene, in addition to 39% by weight of o-dichlorobenzene, and the remainder consists of p-dichlorobenzene, as well as small amounts (less than 5%) of impurities, such as mono-, tri, tetra-, penta- and hexachlorobenzenes and also traces of other chlorinated aromatic compounds or chlorinated aliphatic compounds (in the following text, dichlorobenzene is also abbreviated to DCB).

This mixture is separated in a tray column, in a first step, into an o-dichlorobenzene fraction which contains the higher-boiling constituents and into a p-dichlorobenzene fraction which contains the lower-boiling constitutents, that is to say, in particular, m-dichlorobenzene. The m-dichlorobenzene concentration is about 5% by weight. o-Dichlorobenzene is separated from higher-boiling impurities, such as tri-, tetra-, penta- and hexa-chlorobenzenes, by distillation in a separate distillation step, either in the same column or in a smaller second column. Virtually pure p-dichlorobenzene (over 99% by weight) is now isolated from the p-dichlorobenzene fraction, which contains about 5% by weight of m-dichlorobenzene, in a tube crystallizer in a second step, a p-dichlorobenzene fraction containing m-dichlorobenzene being obtained with a meta-dichlorobenzene concentration of about 30%.

| 2nd step (crystallization at 30 to 40° C.) | m-DCB | o-DCB | p-DCB |
|---|---|---|---|
| Feed material | 5.1 | 0.3 | 94.6 |
| m-Dichlorobenzene concentrate | 30.0 | 1.8 | 68.2 |
| p-Dichlorobenzene crystals | trace | 0.5 | 99.5 |

Further concentration of this fraction containing m-dichlorobenzene is now carried out in a third step in another tube crystallizer.

| 3rd step (crystallization at −30° C.) | m-DCB | o-DCB | p-DCB |
|---|---|---|---|
| Feed material | 30.0 | 1.80 | 68.2 |
| m-Dichlorobenzene concentrate | 77.65 | 3.17 | 19.18 |
| p-Dichlorobenzene crystals | 18.3 | 1.44 | 80.26 |

The m-dichlorobenzene concentrates containing over 70% by weight are concentrated to a m-dichlorobenzene concentrate containing about 95% of m-dichlorobenzene in a 4th step, a distillation step. (the reflux ratio is abbreviated to R/E).

| Columns: 250 actual trays; R/E: 80 or 200 actual trays; R/E: 150 | m-DCB | o-DCB | p-DCB |
|---|---|---|---|
| Feed material | 77.5 | 3.17 | 19.18 |
| Product from the top of the column | 95.0 | not detectable | 5.0 |
| Product from the bottom of the column | 63.18 | 5.91 | 30.91 |

Further concentration of the m-dichlorobenzene concentrate with a concentration of about 95% is carried out in a 5th step, a low temperature crystallization.

| 5th step Crystallization temperature: −30° C. | m-DCB | o-DCB | p-DCB |
|---|---|---|---|
| Feed material | 95.0 | less than 0.1 | 5.0 |
| m-Dichlorobenzene concentrate | 99.5 | — | 0.5 |
| Dichlorobenzene crystals | 90.0 | less than 0.1 | 10.0 |

The examples which follow show that one can vary the concentration as well as the procedure of individual steps:

| Variants in step 3: (crystallization) Crystallization at about −30° C. | m-DCB | o-DCB | p-DCB |
|---|---|---|---|
| Feed material | 40.0 | 1.6 | 58.4 |
| m-Dichlorobenzene concentrate | 80.0 | 3.5 | 16.5 |
| p-Dichlorobenzene crystals | 13.6 | 0.4 | 86.0 |

| Crystallization at −30° C. | m-DCB | o-DCB | p-DCB |
|---|---|---|---|
| Feed material | 47.9 | 6.0 | 46.1 |
| m-Dichlorobenzene concentrate | 75.0 | 6.25 | 18.75 |
| p-Dichlorobenzene crystals | 29.8 | 5.8 | 64.4 |

Using 30% strength m-dichlorobenzene as the starting material (step 3) the crystallization can lead to 75% strength m-dichlorobenzene in 2 steps, a fraction with a m-dichlorobenzene concentration of 40–50% precipitating intermediately.

| Variants in step 4 (distillation) Columns with 200 actual trays; R/E = 180 | m-DCB | o-DCB | p-DCB |
|---|---|---|---|
| Feed material | 75.0 | — | 25.0 |
| Product from the top of the column | 95.06 | — | 4.94 |
| Product from the bottom of the column | 54.92 | — | 45.08 |

| Columns with 200 actual trays; R/E = 200 | m-DCB | o-DCB | p-DCB |
|---|---|---|---|
| Feed material | 70.1 | 4.9 | 25.0 |
| Top of the column | 96.0 | not detectable | 4.0 |
| Bottom of the column | 55.1 | 7.8 | 37.1 |

| Columns with 200 actual trays; R/E = 180 | m-DCB | o-DCB | p-DCB |
|---|---|---|---|
| Feed material | 70.1 | 4.9 | 25.0 |
| Top of the column | 95.8 | not detectable | 4.2 |
| Bottom of the column | 54.9 | 7.9 | 37.2 |

| Columns with 400 actual trays; R/E = 50 | m-DCB | o-DCB | p-DCB |
|---|---|---|---|
| Feed material | 70.1 | 4.9 | 25.0 |
| Top of the column | 94.3 | not detectable | 5.7 |
| Bottom of the column | 55.4 | 8.0 | 36.6 |

| Columns with 300 actual trays; R/E = 60 | m-DCB | o-DCB | p-DCB |
|---|---|---|---|
| Feed material | 70.1 | 4.9 | 25.0 |
| Top of the column | 94.5 | not detectable | 5.5 |
| Bottom of the column | 55.3 | 8.0 | 36.7 |

| Variants in step 5 (crystallization or distillation) Crystallization temperature: −28° C. | m-DCB | o-DCB | p-DCB |
|---|---|---|---|
| Feed material | 94.0 | less than 0.1 | 6 |
| m-Dichlorobenzene concentrate | 99.0 | — | 1 |
| Spent liquor from the crystallization | 89.91 | less than 0.1 | 10.09 |

All the crystallization operations are carried out in steel tube crystallizers.

Step 5 can also be carried out in a column with the aid of distillation, as the following examples show:

| Columns with 200 actual trays, R/E = 162 | m-DCB | o-DCB | p-DCB |
|---|---|---|---|
| Feed material | 96.0 | not detectable | 4.0 |
| Top of the column | 99.1 | — | 0.9 |

-continued

| Bottom of the column | 84.9 | — | 15.1 |
|---|---|---|---|
| Columns with 250 actual trays, R/E = 78 | | | |
| | m-DCB | o-DCB | p-DCB |
| Feed material | 94.65 | not detectable | 5.35 |
| Top of the column | 99.05 | — | 0.95 |
| Bottom of the column | 85.0 | not detectable | 15.0 |
| Columns with 300 actual trays, R/E = 51 | | | |
| | m-DCB | o-DCB | p-DCB |
| Feed material | 96.0 | not detectable | 4.0 |
| Top of the column | 99.05 | — | 0.95 |
| Bottom of the column | 84.9 | — | 15.1 |
| Columns with 400 actual trays, R/E = 41 | | | |
| | m-DCB | o-DCB | p-DCB |
| Feed material | 96.0 | not detectable | 4.0 |
| Top of the column | 99.1 | — | 0.9 |
| Bottom of the column | 84.9 | — | 15.1 |

What is claimed is:

1. A process for separating ortho-, meta-, and/or para-dichlorobenzene from an isomeric mixture thereof which comprises:
   A. in a first step distilling said isomeric mixture to distill over meta- and/or para-dichlorobenzene to leave behind ortho-dichlorobenzene which is separated off as bottoms product;
   B. in a second step, cooling the distillate from step A to a temperature of 10° to 40° C. whereby para-dichlorobenzene as a solid phase is obtained and separating the said solid phase from liquid phase with which it is in admixture;
   C. in a third step, further cooling said liquid phase from step B to a temperature of −40° to −5° C. whereby to precipitate a second solid phase and separating said second solid phase from the liquid phase with which it is in admixture;
   D. in a fourth step, distilling the liquid phase from step C whereby to obtain an isomeric mixture as bottoms and an isomeric mixture as distillate; and
   E. removing m-dichlorobenzene from the distillate by step D by:
      1. Cooling the distillate to a temperature of −25° to −40° C. whereby m-dichlorobenzene precipitates as a solid and removing solid m-dichlorobenzene from the liquid and recycling the remaining liquid to the distillation of step D; or
      2. Further distilling the distillate of step D to remove m-dichlorobenzene as overhead and recycling the bottoms of such distillation to step D.

2. A process according to claim 1 wherein m-dichlorobenzene is removed from the distillate of step D by cooling the distillate to a temperature of −25° to −40° C. whereby m-dichlorobenzene precipitates as a solid and the solid m-dichlorobenzene is separated from the liquid and the liquid is fed to the distillation of step D.

3. A process according to claim 1 wherein m-dichlorobenzene is removed from the distillate of step D by further distilling the distillate of step D to remove m-dichlorobenzene as overhead and the bottoms of the distillation are recycled to step D.

4. A process according to claim 1 wherein step A is performed in a distillation column having 130 to 250 trays.

5. A process according to claim 1 wherein the distillation of step D is performed using a distillation column having 70 to 300 trays.

* * * * *